(12) United States Patent
Ter-Ovanesyan et al.

(10) Patent No.: US 6,359,190 B1
(45) Date of Patent: Mar. 19, 2002

(54) DEVICE FOR MEASURING THE VOLUME OF A BODY CAVITY

(75) Inventors: Evgeny Ter-Ovanesyan, Cincinnati; Donald C. Roe, West Chester, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/643,008

(22) Filed: Aug. 21, 2000

Related U.S. Application Data (63) Continuation-in-part of application No. 09/599,622, filed on Jun. 22, 2000, which is a continuation-in-part of application No. 09/342,784, filed on Jun. 29, 1999, and a continuation-in-part of application No. 09/342,289, filed on Jun. 29, 1999, now Pat. No. 6,266,557, which is a continuation-in-part of application No. 09/107,561, filed on Jun. 29, 1998, now Pat. No. 6,149,636, and a continuation-in-part of application No. 09/106,225, filed on Jun. 29, 1998, now Pat. No. 6,186,991, which is a continuation-in-part of application No. 09/107,561, said application No. 09/643,008.

(60) Provisional application No. 60/090,993, filed on Jun. 29, 1998.

(51) Int. Cl.[7] .......................... A61F 13/42; G08B 23/00
(52) U.S. Cl. ...................... 604/361; 600/449; 340/573; 128/886
(58) Field of Search ................... 604/361, 22; 600/449; 340/573; 364/413.02, 413.25, 413.13, 413.15; 128/885, 886, DIG. 25

(56) References Cited

U.S. PATENT DOCUMENTS

| 2,127,538 A | 8/1938 | Seiger | 128/238 |
| 2,926,667 A | 3/1960 | Burger et al. | 128/285 |

(List continued on next page.)

FOREIGN PATENT DOCUMENTS

| DE | 39 21 784 A1 | 1/1991 | ............. A61B/5/00 |
| EP | 0 286 374 | 10/1988 | ............. A61B/5/00 |

(List continued on next page.)

OTHER PUBLICATIONS

Une application de l'analyse spectrale dans le traitement des signaux electrosplanchnographiques, Medical and Biological Engineering, Mar. 1975 (XP–002150656). No English Translation Provided.

Ein portables System zur kontinuierlichen strebfreien Aufzeichnung der Harnblasenmotorik, A portable system for continuous Stress–Free Measurement of Bladder Function, Biomed. Technik, 30 (1985), 85–90 (XP 000601891). No English Translation Provided.

Beautelspacher et al., "Ein protables System zur kontinuierlichen stressfreien Aufzeichnung der Harnblasenmotorik", BIOMEDIZINISCHE TECHNIK, vol. 30, No. 4, Apr. 1985, pp. 85–90. No English Translation Provided.

*Primary Examiner*—John G. Weiss
*Assistant Examiner*—Michael Bogart
(74) *Attorney, Agent, or Firm*—David M. Weirich; Michael P. Hayden; Ken K. Patel (57) ABSTRACT

A device adapted to measure the volume of a body cavity including a base, a sensor adapted to detect when a body cavity of the wearer reaches a predetermined volume and a signal mechanism. The sensor is moveably mounted on the base so as to facilitate aiming of the sensor toward the body cavity. The signal mechanism is adapted to provide a signal once the predetermined body cavity volume is reached. Alternatively, the device may comprise a first sensor and a second sensor which are oriented differently toward the body cavity and which each measure a distance between the front wall and the back wall of the body cavity. The device also includes a signal mechanism which provides a once a predetermined volume of the body cavity is reached, wherein the volume is calculated based on the greater of the distances measured between the front wall and the back wall of the body cavity.

22 Claims, 4 Drawing Sheets

U.S. PATENT DOCUMENTS

| | | | | |
|---|---|---|---|---|
| 3,650,275 | A | 3/1972 | Von Der Mozel | 128/407 |
| 3,814,101 | A | 6/1974 | Kozak | 128/287 |
| 3,881,491 | A | 5/1975 | Whyte | 128/287 |
| 3,921,232 | A | 11/1975 | Whyte | 5/91 |
| 3,987,792 | A | 10/1976 | Hernandez et al. | 128/284 |
| 4,022,211 | A | 5/1977 | Timons et al. | 128/287 |
| 4,246,900 | A | 1/1981 | Schröder | 128/287 |
| 4,335,722 | A | 6/1982 | Jackson | 128/285 |
| 4,341,120 | A * | 7/1982 | Anderson | 604/618 |
| 4,356,818 | A | 11/1982 | Macias et al. | 128/138 |
| 4,401,712 | A | 8/1983 | Morrison | 428/289 |
| 4,636,474 | A | 1/1987 | Ogura et al. | 435/291 |
| 4,657,537 | A | 4/1987 | Zimmerer | 604/360 |
| 4,681,577 | A | 7/1987 | Stern et al. | 604/378 |
| 4,705,050 | A | 11/1987 | Markham | 128/749 |
| 4,732,930 | A | 3/1988 | Tanaka et al. | 524/742 |
| 4,747,166 | A | 5/1988 | Kuntz | 4/144.1 |
| 4,753,645 | A | 6/1988 | Johnson | 604/378 |
| 4,754,264 | A | 6/1988 | Okada et al. | 340/573 |
| 4,776,331 | A | 10/1988 | Simjian | 128/169 |
| 4,778,459 | A | 10/1988 | Fuisz | 604/378 |
| 4,787,896 | A | 11/1988 | Houghton et al. | 604/385.1 |
| 4,790,836 | A | 12/1988 | Brecher | 604/359 |
| 4,796,014 | A | 1/1989 | Chia | 340/573 |
| 4,842,593 | A | 6/1989 | Jordan et al. | 604/360 |
| 4,852,578 | A | 8/1989 | Companion et al. | 128/661.03 |
| 4,968,312 | A | 11/1990 | Khan | 604/388.1 |
| 4,981,465 | A | 1/1991 | Ballan et al. | 600/32 |
| 5,002,541 | A | 3/1991 | Conkling et al. | 604/319 |
| 5,100,933 | A | 3/1992 | Tanaka et al. | 523/300 |
| 5,103,835 | A | 4/1992 | Yamada et al. | 128/734 |
| 5,118,607 | A | 6/1992 | Bignami et al. | 435/7.1 |
| 5,181,905 | A | 1/1993 | Flam | 602/41 |
| 5,264,830 | A | 11/1993 | Kline et al. | 340/604 |
| 5,330,459 | A | 7/1994 | Lavon et al. | 604/385.1 |
| 5,341,127 | A | 8/1994 | Smith | 340/604 |
| 5,342,343 | A | 8/1994 | Kitaoka et al. | 604/385.2 |
| 5,411,548 | A | 5/1995 | Carman | 607/138 |
| 5,416,469 | A | 5/1995 | Colling | 340/573 |
| 5,468,236 | A | 11/1995 | Everhart et al. | 604/361 |
| 5,520,674 | A | 5/1996 | Lavon et al. | 604/385.1 |
| 5,558,655 | A | 9/1996 | Jezzi et al. | 604/378 |
| 5,568,128 | A | 10/1996 | Nair | 340/604 |
| 5,582,604 | A | 12/1996 | Ahr et al. | 604/385.1 |
| 5,607,417 | A | 3/1997 | Batich et al. | 604/890.1 |
| 5,641,562 | A | 6/1997 | Larson et al. | 442/394 |
| 5,643,241 | A | 7/1997 | Ahr et al. | 604/385.1 |
| 5,649,914 | A | 7/1997 | Glaug et al. | 604/361 |
| 5,653,862 | A | 8/1997 | Parris | 205/777.5 |
| 5,658,268 | A | 8/1997 | Johns et al. | 604/361 |
| 5,678,564 | A | 10/1997 | Lawrence et al. | 128/761 |
| 5,681,298 | A | 10/1997 | Brunner et al. | 604/361 |
| 5,702,376 | A | 12/1997 | Glaug et al. | 604/361 |
| 5,702,428 | A | 12/1997 | Tippey et al. | 607/41 |
| 5,722,931 | A | 3/1998 | Heaven | 660/29 |
| 5,728,125 | A | 3/1998 | Salinas | 604/361 |
| 5,733,272 | A | 3/1998 | Brunner et al. | 604/359 |
| 5,736,590 | A | 4/1998 | Rasmussen | 523/113 |
| 5,755,674 | A | 5/1998 | Watson | 600/587 |
| 5,760,694 | A | 6/1998 | Nissim et al. | 340/604 |
| 5,769,834 | A | 6/1998 | Reiter et al. | 604/385.1 |
| 5,797,892 | A | 8/1998 | Glaug et al. | 604/361 |
| 5,876,393 | A | 3/1999 | Ahr et al. | 604/387 |
| 6,027,449 | A * | 2/2000 | Mazess et al. | 604/449 |

FOREIGN PATENT DOCUMENTS

| | | | | |
|---|---|---|---|---|
| EP | 0 612 520 | A2 | 8/1994 | A61K/9/52 |
| EP | 0 804 912 | | 11/1997 | A61F/13/15 |
| EP | 0 804 913 | | 11/1997 | A61F/13/15 |
| EP | 0 804 914 | A1 | 11/1997 | A61F/13/15 |
| EP | 0 804 915 | | 11/1997 | A61F/13/15 |
| EP | 0 804 916 | | 11/1997 | A61F/13/15 |
| EP | 0 804 917 | | 11/1997 | A61F/13/15 |
| EP | 0 806 194 | | 11/1997 | A61F/13/15 |
| EP | 0 806 195 | | 11/1997 | A61F/13/15 |
| EP | 0 815 818 | A1 | 1/1998 | A61F/13/15 |
| EP | 0 815 821 | A2 | 1/1998 | A61F/13/15 |
| WO | WO-86/06606 | * | 11/1986 | A61B/8/00 |
| WO | WO 86/06606 | A1 | 11/1986 | |
| WO | WO 88/03390 | A1 | 5/1988 | |
| WO | WO-88/03390 | * | 5/1988 | A61B/10/00 |
| WO | WO 92/02005 | A | 2/1992 | G08F/8/00 |
| WO | WO 94/24974 | | 11/1994 | A61F/13/15 |
| WO | WO 95/00089 | | 1/1995 | A61F/13/15 |
| WO | WO 95/00090 | | 1/1995 | A61F/13/15 |
| WO | WO 95/32697 | | 12/1995 | A61F/13/15 |
| WO | WO 95/32698 | | 12/1995 | A61F/13/15 |
| WO | WO 96/14813 | | 5/1996 | A61F/5/48 |
| WO | WO 96/20681 | | 7/1996 | A61F/13/15 |
| WO | WO 97/16149 | | 5/1997 | A61F/13/42 |
| WO | WO 97/24150 | | 7/1997 | A61L/15/62 |
| WO | WO 97/32542 | | 9/1997 | A61F/2/00 |
| WO | WO 97/42613 | | 11/1997 | G08B/21/100 |
| WO | WO 97/45082 | | 12/1997 | A61F/13/15 |
| WO | WO 98/18505 | | 5/1998 | A61L/15/60 |
| WO | WO 98/22063 | | 5/1998 | A61F/13/15 |
| WO | WO 98/29079 | | 7/1998 | A61F/13/15 |
| WO | WO 98/29501 | | 7/1998 | C08L/1/28 |
| WO | WO 99/07317 | | 2/1999 | A61F/13/15 |

* cited by examiner

DEVICE FOR MEASURING THE VOLUME OF A BODY CAVITY

CROSS REFERENCE TO RELATED APPLICATIONS

This application is a continuation-in-part of prior application U.S. Ser. No. 09/599,622 filed Jun. 22, 2000, which is a continuation-in-part of prior application U.S. Ser. No. 09/342,784 filed on Jun. 29, 1999, which is a continuation-in-part of prior application U.S. Ser. No. 09/107,561 filed on Jun. 29, 1998 now U.S. Pat. No. 6,149,636, and U.S. Ser. No. 09/106,225 filed on Jun. 29, 1998 now U.S. Pat. No. 6,186,991, and a non-provisional filing of prior provisional application U.S. Ser. No. 60/090,993 filed Jun. 29, 1998. This application is also a continuation-in-part of U.S. Ser. No. 09/342,289 filed on Jun. 29, 1999 is now U.S. Pat. No. 6,266,554, which is a continuation-in-part of prior application U.S. Ser. No. 09/107,561 filed on Jun. 29, 1998.

FIELD OF THE INVENTION

The present invention relates to devices having a sensor adapted to measure the volume of a body cavity, such as a bladder, and to provide a signal to the user, wearer, or caregiver when the body cavity volume reaches a predetermined threshold.

BACKGROUND OF THE INVENTION

Today, devices adapted to measure bladder volume are widely used for diagnostic purposes in the medical profession, such as the urology field. Additionally, bladder volume measurement devices have been developed for continence training applications. Some of these devices provide a complete two or three-dimensional image of the bladder using ultrasonic transducers that are rotated or moved in a pattern within an ultrasound scanning head. These devices have the disadvantage of being large, heavy, complex and extremely costly and require significant signal processing and analysis capability. Another approach provides measures of bladder volume via arrays of ultrasonic transducers positioned on a subject's body in an area or pattern in proximity to the bladder (e.g., around the waist of the wearer). In such devices, the array determines a number of points on the front and back walls of the bladder and fits a curve to the points to define a cross-section. This approach has the limitation of requiring significant computational resources due to the need for the complex curve-fitting analysis of the transducer data. Yet another approach involves the use of a single ultrasonic transducer positioned on the wearer's abdomen in proximity to the bladder. In this device, an ultrasound pulse is transmitted to and through the bladder and the volume is calculated by comparing the time difference of the echoes from the front and rear walls of the bladder, A key disadvantage of this device is the difficulty in aiming the ultrasonic transducer at the bladder (i.e., the aim varies depending on application of the device). The entire device must be reapplied or shifted on the wearer to correct a non-optimal initial aim. Additionally, none of the known bladder volume measurement devices are easily or comfortably wearable by the subject.

Accordingly, it would be advantageous to provide a body cavity volume monitor which is comfortable to wear. It would also be advantageous to provide a body cavity volume monitor which can be adjusted to improve performance after the device is applied to the wearer. Further, it would be advantageous to provide a body cavity volume monitor which is configured such that even if it is displaced or not optimally aligned, an accurate measurement can be obtained.

SUMMARY OF THE INVENTION

In order to resolve the shortcomings of the prior art, the present invention provides a device or article which includes a base, a sensor adapted to detect when a body cavity of the wearer reaches a predetermined volume and a signal mechanism. The sensor is moveably mounted on the base so as to facilitate aiming of the sensor toward the body cavity. The signal mechanism is adapted to provide a signal to a wearer, a caregiver or an element of the article once the predetermined body cavity volume is reached.

In an alternative embodiment, the present invention provides a device adapted to measure the volume of a body cavity comprising a first sensor and a second sensor. The first sensor has a first orientation toward the body cavity and is adapted to measure a first distance between the front wall and the back wall of the body cavity. The second sensor has a second orientation toward the body cavity which is different from the first orientation and is adapted to measure a second distance between the front wall and the back wall of the body cavity. The device also includes a signal mechanism which provides a signal to a wearer or a caregiver once a predetermined volume of the body cavity is reached, wherein the predetermined volume is calculated based on the greater of the first and second distances between the front wall and the back wall of the body cavity.

DETAILED DESCRIPTION OF THE INVENTION

Figure 1:
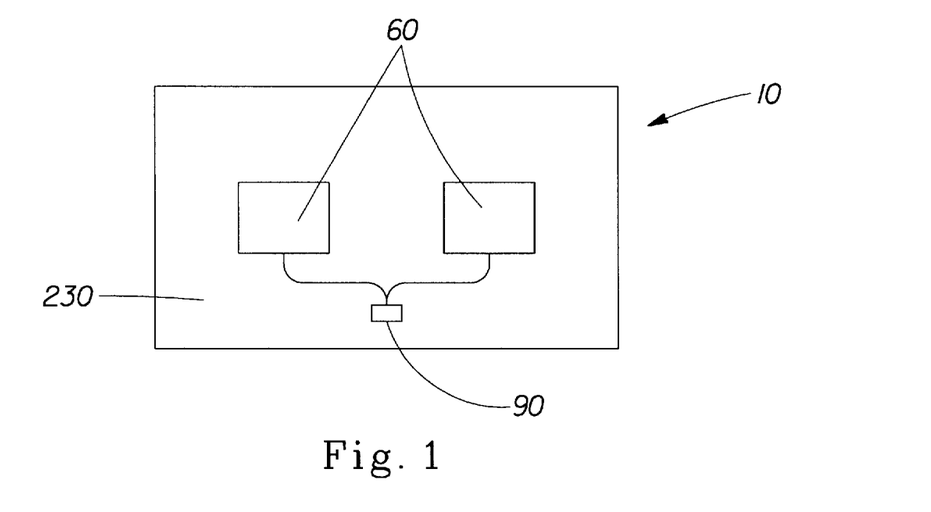
FIG. 1 is a plan view of one embodiment of the device of the present invention.

The present invention is directed to a device which can be adapted to measure the volume of a body cavity, such as a human bladder or rectum. The device 10 of the present invention, as shown in FIG. 1, includes a base 230 and at least one sensor 60 adapted to provide a measure of the volume of a body cavity, or a parameter associated with or correlated to the volume, such as a width, length, or depth of the cavity. The device further includes at least one signal mechanism 90. One advantage of the device 10 over the prior art is that the device 10 is designed to reduce the need for precise positioning of the sensor 60 over the target body cavity during the initial application of the device. Further, in one embodiment, the device 10 is designed to permit relatively simple aiming of the sensor 60 toward the body cavity after application and during use.

Figure 2:
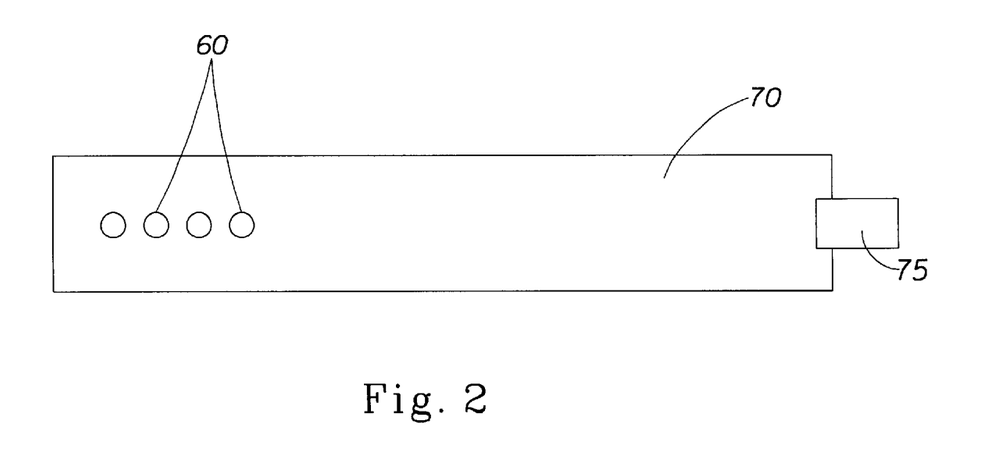
FIG. 2 is a plan view of an embodiment of the present invention including a belt.
Figure 3:
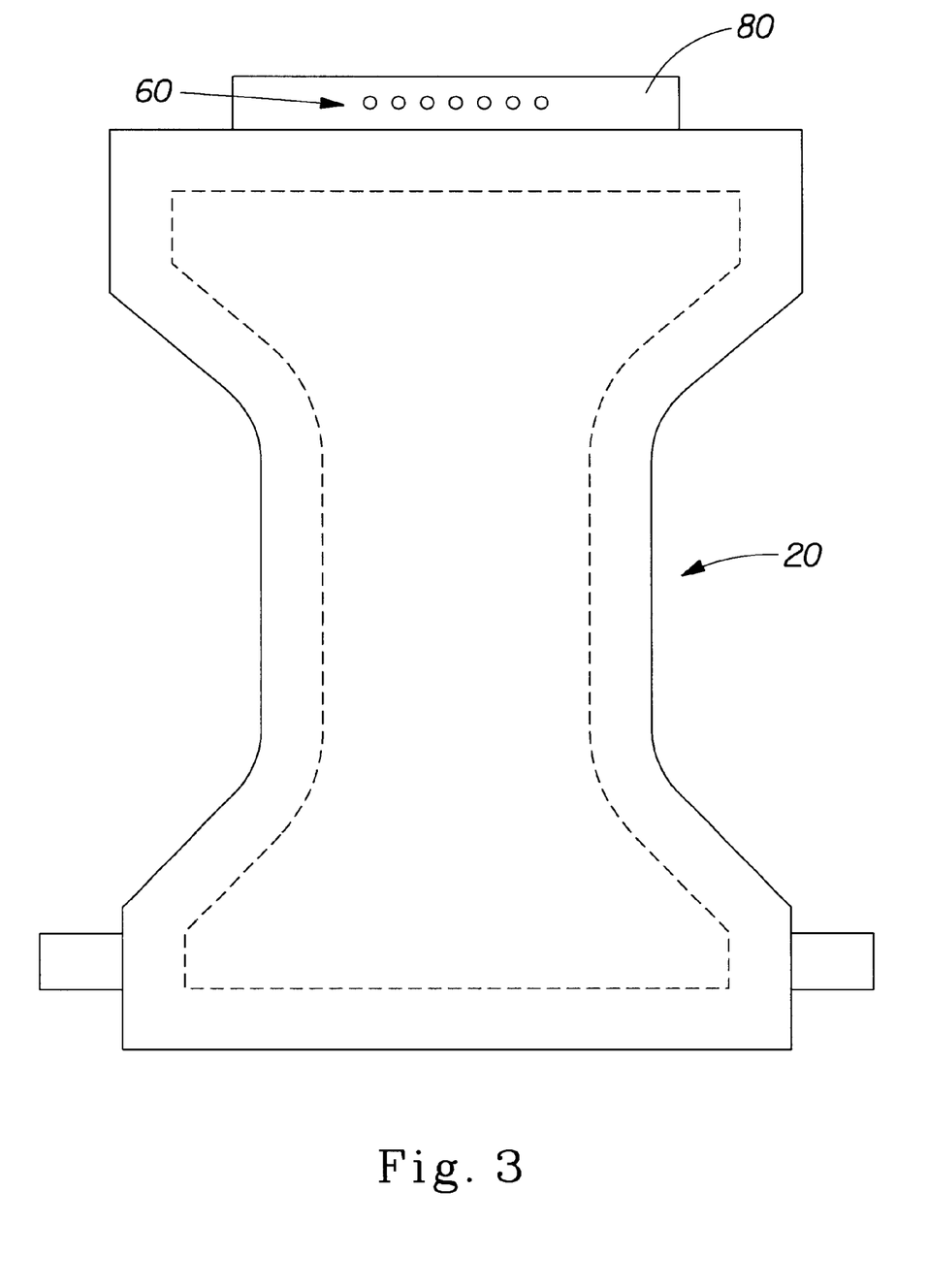
FIG. 3 is a plan view of an embodiment of the present invention which includes a disposable absorbent article.
Figure 4:
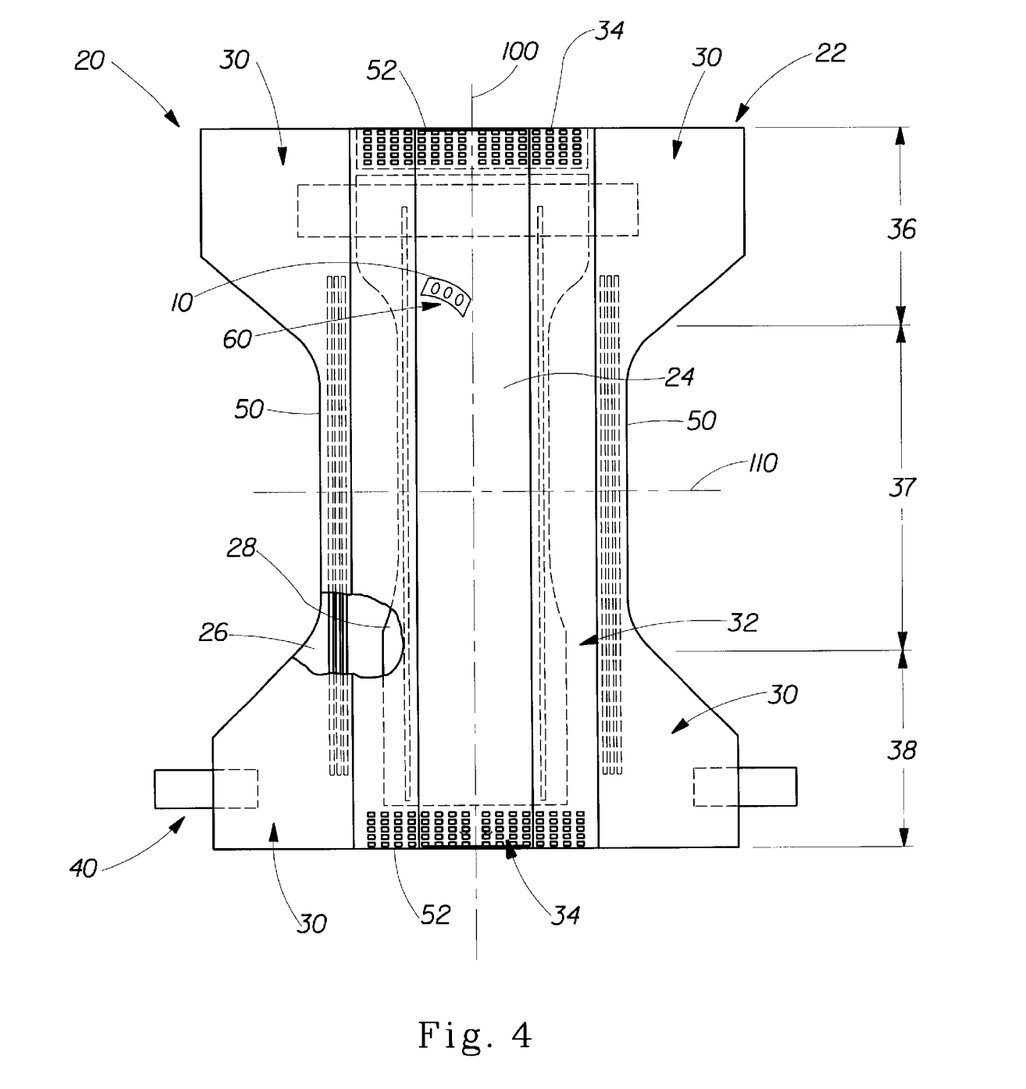
FIG. 4 is a plan view of an alternative disposable absorbent article embodiment of the present invention in a flat-out state with portions of the structure being cut-away to more clearly show the construction of the article, wherein the article is a diaper.

The device 10 is preferably wearable by a subject such as a human or other animal. For example, the device 10 or a component thereof, such as the sensor 60, may be joined directly to the skin of the wearer or may be mounted on a durable or disposable belt or strap system, etc. An exemplary belt embodiment of the device 10 including the sensor 60 is shown in FIG. 2, and is described in more detail below. The device 10 may alternatively operatively connected to or disposed within disposable absorbent article, such as a diaper, insert, training pant, swim pant, or waste bag, such that the sensor 60 is maintained in intimate contact with the skin of the wearer in the proximity of the body cavity of interest. Examples of disposable absorbent article embodiments are shown in FIGS. 3–4 and are described in more detail below.

The device 10 may be disposed in any configuration on the wearer so long as the sensor 60 can be maintained for a sufficient period of time in close proximity with the wearer's skin. Preferably, the device 10 is configured and positioned such that the sensor 60 is at least operatively connected to the wearer's body. For the purposes of the present invention, the term "operatively connected" refers to a configuration in which the sensor 60 may communicate (i.e., transmit or receive signals, such as ultrasonic waves or pulses), to or from the target body cavity of the wearer. The communication may be performed by any suitable means such as an electrical connection via a conductive wire or member, via a transmitted signal such as radio frequency, infrared or another transmitted frequency communication, etc. Alternatively, the sensor 60 may be operatively connected such that the communication is via a mechanical connection such as physical contact or a pneumatic or a hydraulic connection. Typically, the sensor should be in intimate or immediate contact with the wearer's skin, although embodiments are contemplated wherein some or all of the device 10 is separated from the wearer's skin by some material or substance. Physical contact of the sensor 60 with the wearer's skin may be achieved, maintained, or enhanced via use of adhesives or body adhering compositions, gels, acoustic conducting materials, and/or elastic forces.

The device 10, including sensor 60 and signal mechanism 90, is adapted to measure the volume of a body cavity, such as the bladder, rectum or colon, and preferably, signal the wearer or caregiver when the volume of the cavity reaches a predefined threshold. For example, in one embodiment, a threshold value for the bladder or rectum which may be relevant to determining the next excretion may be about 80% of the daytime maximum volume or the minimum observed micturition or defecation volume. It may be desirable to measure certain characteristics of the bladder or other body cavity which correspond to a certain volume. For example, the device 10 may be adapted to measure the distance between the walls of the cavity, e.g. the bladder walls, and calculate or otherwise determine the approximate volume of the cavity. In such cases, the device 10 itself may perform the calculations or may merely send the data to another device such as a computer which can perform the desired calculations.

The device 60 may comprise any number of sensors 60 or signal mechanisms 90. The sensors 60 may detect the same or different signals from the same or different sources. The sensor(s) 60 and signal mechanism(s) 90 may include components that are located inside, external to and/or separate from the device 10. For example, the device 10 may include a sensor 60 inside a wearable article that measures the volume of the wearer's bladder and a sensor 60 external to the article that detects motion, tension or muscle activity in the abdomen of the wearer. The device 10 may also or alternatively include components other than the sensing elements inside, external to and/or separate from the article.

For example, the device 10 may include a transmitter that is external to the device 10 and which transmits a signal to another part of the device 10 that is joined to or disposed on the device 10.

In one embodiment of the present invention, the sensor 60 includes an ultrasonic transducer. In a preferred embodiment, the ultrasonic transducer is a piezoelectric transducer, which is pulsed by application of intermittent electric current, causing it to vibrate for a short time at its resonant frequency. An exemplary suitable ultrasonic transducer having a 19 mm diameter and operating at 3.5 MHz is available from the American Piezoceramic Company. In such embodiments, the sensor 60 is preferably releasably secured to the skin of the wearer in order to transmit and/or receive signals, such as ultrasonic waves or pulses, to and/or from a target body cavity of the wearer. For example, the sensor 60 may be placed as close as possible to the wearer's bladder so that the transducer may effectively transmit and receive signals (i.e., echoes) to and from the bladder walls. If the sensor 60 is not self-adhesive, an electroconductive, adhesive gel, body adhering composition, or acoustic coupling medium may be placed on the electrode of the skin contact probe before it is placed on the skin to enhance ultrasonic pulse transmission to the body. In such embodiments, the sensor 60 may be placed on the wearer by the caretaker, or may be integral with an article, such as a diaper or belt, such that they are automatically aligned and attached to the wearer's skin near the body cavity when the article is placed on the wearer.

FIG. 2 shows one embodiment of the present invention wherein the device 10 is associated with a belt 70. During use, the belt 70 is preferably fitted or secured around at least a portion of the wearer's body generally corresponding to the location of the bladder, colon or other body cavity of interest. At least a portion of the belt 70 may be elastically extensible so as to accommodate local changes in the wearer's dimensions and to provide a sufficiently snug fit to hold the sensor 60 in the target location while the belt 70 is worn.

The belt 70 may be secured around the wearer's abdomen by any fastening system 75 as known in the art, including adhesive tapes, topical adhesives, mechanical fasteners such as hook and loop fasteners, buttons, and the like. Alternatively, or in addition, any portion of the belt 70 or device 10 or any of the sensors 60 may be affixed to the wearer directly via the use of topical adhesives or other body adhering compositions, which are described in more detail below. In any case, the belt 70 preferably holds at least one sensor 60 in a position such that the sensor 60 is operatively connected to the wearer's body.

Body adhering compositions suitable for use in the present invention may be in any form, including, but not limited to gels, lotions, films, webs or the like. Some exemplary body adhesives include adhesives, gelatin, petrolatum, waxes such as silicone or petroleum waxes, oils such as silicone or petroleum based oils, skin care compositions or ingredients thereof. Other topical adhesives include, but are not limited to, hydrogel or hydrocolloid adhesives such as acrylic based polymeric adhesives, and the like. (Some exemplary hydrogel and/or hydrocolloid adhesives are disclosed in U.S. Pat. Nos. 4,231,369; 4,593,053; 4,699,146; 4,738,257; and 5,726,250; each of which is incorporated by reference herein.) The topical adhesives may also include any "medical adhesive" which is compatible for use with biological tissue, such as skin. Acrylic medical adhesives suitable for use as body adhering compositions, include adhesives available from Adhesive Research, Inc., of Glen Rock, Pa., under the designations MA-46, MA-312, "MTTM" High MVTR adhesive, and AS-17. Rubber-based medical adhesives, such as SB-2 from Adhesive Research Inc. may also be suitable. Other is exemplary adhesives include Dow Coming Medical Adhesive (Type B) available from Dow Coming, Midland, Mich.; "MEDICAL ADHESIVE" from Hollister Inc., of Libertyville, Ill.; 3M Spray Adhesives #79, 76, 77 and 90 available from the 3M Corp. of St. Paul, Minn.; and "MATI-SOL" liquid adhesive available from Ferndale Laboratories of Ferndale, Mich. Other medical adhesives are described in U.S. Pat. Nos. 4,078,568; 4,140,115; 4,192,785; 4,393,080; 4,505,976; 4,551,490; 4,768,503 and polyacrylate and polymethacrylate hydrogel adhesives are disclosed in U.S. Pat. Nos. 5,614,586 and 5,674,275; the disclosure of each of which is incorporated by reference herein. Yet another exemplary adhesive comprising polyvinyl pyrollidone and a multi-functional amine-containing polymer is disclosed in WO 94/13235A1. (The disclosure of each of these references is incorporated herein by reference.) Alternative body adhering means which may be used in place of or in addition to those described above include static electricity, suction and the like. Typically, it is preferred that the body adhering composition permit vapors to pass (i.e., breathable), be compatible with the skin and otherwise skin friendly.

Generally, to obtain the desired characteristics, the body adhering composition may comprise: from 0.5 to 20%, preferably 5% to 15%, by weight of a macromolecular polymeric substance or a mixture of such substances soluble or swellable in the below mentioned plasticizer(s). As not limiting examples such macromolecular or polymeric substances can be natural and/or synthetic such as natural gums or derivatives such as natural gums and gelatins, their derivatives and alginates; polyacrylics; polyvinyl alcohol; polyethylene oxide; polyvinylpyrrolidon (PVP) or polyvinylethers, their copolymers and derivatives; cellulose derivatives; Block Copolymer Thermoplastic Elastomers and preferably Styrenic block Copolymers and more preferably the hydrogenated grades Styrol/Ethylene-Butylene/Styrol (SEBS), Styrene/Isoprene/Styrene (SIS), and Styrol/Ethylene-Propylene/Styrol (SEPS). Further, preferred body adhesive compositions may comprise from 45 to 99.5% by weight, preferably from 51 to 99.5% by weight, of a plasticizing substance or a mixture of plasticizing substances, which are liquid at room temperature. As non-limiting examples the plasticizer can be water, various alcohols (like in particular glycerol), gylcols and their ethers, polyglycols, liquid polybutenes, esters such phtalates, adipates, stearates, palmitates, sebacates, or myristates, natural or synthetic oils such as vegetable oils, mineral oils, or combinations thereof. Further, the body adhesive may include from 0% to 50% by weight of the composition, preferably 0% to 600% by weight of the macromolecular polymeric substance, of a tackifying resin whose main scope is to tailor the Tg especially in systems based on synthetic polymers. Also, preferred body adhesives may include from 0 to 10% and more preferably from 0 to 5% by weight of substances for facilitating and stabilizing the gel and the gel forming process both of hydrophilic or hydrophobic liquid plasticizers. These may be for oily systems, e.g., the fatty acids of $C_8$ to $C_{22}$, their metallic salts and their polyoxo-derivatives; lanolin derivatives; silica; bentonite, montmorillonite and their derivatives; polyamides, waxes or mixtures thereof.

Common additives known in the art as preservative, antioxidants, anti UV, pigments, mineral fillers, rheology modifiers and the like may also be included generally in quantities up to about 10% each. Also, when chemical crosslinks are formed in the system, a cross-linking agent may be present, preferably in quantities up to 5% by weight. Chemical crosslinking can be formed also by mutual neutralization of polymers having different functionalities as in the reaction between acid polyacrylics and polysaccharides.

Suitable skin care compositions which may be used as, with, or in place of the body adhesives include Category I actives as defined by the U.S. Federal Food and Drug Administration's (FDA) Tentative Final Monograph on Skin Protectant Drug Products for Over-the-Counter Human Use, which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use tentative final monograph on skin protectant drug products for over-the-counter human use, which presently include: live yeast cell derivatives, aldioxa, aluminum acetate, microporous cellulose, cholecalciferol, colloidal oatmeal, cysteine hydrochloride, dexpanthenol, Peruvian balsam oil, protein hydrolysates, racemethionine, sodium bicarbonate, Vitamin A, and the like. Many of the FDA monographed skin care ingredients are currently utilized in commercially available skin care products, such as "A AND D" Ointment, "VASELINE" Petroleum Jelly, "DESITIN" Diaper Rash Ointment and Daily Care Ointment, "GOLD BOND" Medicated Baby Powder, "AQUAPHOR" Healing Ointment, "BABY MAGIC" Baby Lotion, "JOHNSON'S ULTRA SENSITIVE" Baby Cream, Johnson's baby lotion, lip balms, etc. Other suitable skin care compositions (e.g., lotions) are described in detail in U.S. Pat. No. 5,643,588; U.S. Pat. No. 5,607,760; U.S. Pat. No. 5,609587; and U.S. Pat. No. 5,635,191; each of these references being incorporated herein by reference.

FIG. 4 shows a plan view of a disposable absorbent article, such as a diaper 20, including the device 10 of the present invention. As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner. In one preferred embodiment of the present invention, the absorbent article is a unitary disposable absorbent article, such as the diaper 20 shown in FIG. 4.). A "unitary" absorbent article refers to absorbent articles which are formed of separate parts united together to form a coordinated entity so that they do not require separate manipulative parts like a separate holder and liner. The term "diaper" refers to an absorbent article generally worn by infants and incontinent persons about the lower torso. The diaper 20 is shown in FIG. 4 in a flat-out, state with portions of the structure being cut-away to more clearly show the construction of the diaper 20. The portion of the diaper 20 which faces the wearer is oriented towards the viewer.

The present invention may also be applicable to other absorbent or non-absorbent articles such as incontinence briefs, incontinence undergarments, absorbent inserts, diaper holders and liners, colostomy bags for a natural or artificial anus, feminine hygiene garments, tampons, bandages, therapeutic wraps, disposable heating pads and the like.

The diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 4 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

Other absorbent article embodiments are disclosed in U.S. Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,897,545 titled "Elastomeric Side Panel for Use with Convertible Absorbent Articles" issued Apr. 27, 1999; U.S. Pat. No. 5,904,673 titled "Absorbent Article With Structural Elastic-Like Film Web Waist Belt" issued May 18, 1999; U.S. Pat. No. 5,931,827 titled "Disposable Pull On Pant" issued Aug. 3, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999. The disclosures of each of these patents is incorporated herein by reference.

In disposable absorbent article embodiments, the sensor 60 may be located in the front waist region 36, the rear waist region 38 or the crotch region 37 of article 20, and may be integral with, disposed adjacent to, joined to, or comprise a portion of the chassis 22, the topsheet 24, the backsheet 26, the absorbent core 28, side panels 30, leg cuffs 32, a waist feature 34, a fastening system 40, the longitudinal 50 or end 52 edges, etc. The sensor 60 may be integral with the article 20, or may be a separate device which can be installed into the article by the caretaker or the wearer. Further, the device 10 or sensor 60 may be completely contained within the article or may have a portion, such as a receiving portion, located in the article such that it will come into contact with the wearer's skin in proximity to the target body cavity and another portion, such as a transmitting portion, located either in the article or outside the article. Alternatively, the device 10 may be external to the article 20 yet operatively connected to some portion of the article 20 such that the device 10 may measure the volume of the wearer's bladder or other body cavity, from a location on the skin external to the article 20 and provide a signal to a controller and/or an actuator. In some embodiments, the sensor 60 may be separate from the article, e.g., separately applied to some portion of the wearer, and/or may have one or more components separate from the article 20.

In another embodiment, as shown in FIG. 3, the article 20 may include an extension 80 comprising one or more sensors 60, such as an array of ultrasonic transducers. The extension 80 of the article 20 generally functions to maintain the position of the sensor(s) 60 over the target body cavity and maintain contact of the sensor(s) 60 with the wearer's skin. The extension 80 may, for example, cover at least a portion of the wearer's abdomen, positioning the sensor(s) 60, on the wearer's abdomen in proximity to the bladder. The extension 80 may be of any suitable shape, size or material, may be elastic or inelastic, and may comprise a fastening system, stiffening elements, or a body-adhering composition, such as a topical adhesive, to maintain alignment of the sensor with the target body cavity.

The device 10 of the present invention may be in the form of a pre-micturition enuresis alarm. In such embodiments, the device may comprise a monitoring system including a piezoelectric transducer that measures the volume of a fluid-filled cavity in the body, such as a bladder or rectum. When electrically stimulated, the piezoelectric transducer preferably sends an ultrasonic pulse into the abdomen. The pulse may be sent out at any pre-defined or random interval. The time delay between ultrasonic pulses reflected by the various layers or components of the abdomen is then detected by the transducer. The signal may be processed so as to calculate the distance between the front and back walls of the bladder or other cavity and to estimate the relative volume of the bladder or other cavity versus a reference state, such as a maximum observed volume or an average volume at micturition (i.e., the device may correlate the distance between the walls of the body cavity to a calculated or known body cavity volume). When a predetermined threshold parameter is met, the system generates a signal which can be sent to the wearer or caregiver or to another system or device which stores the information or otherwise responds to the signal. More specifically, a pre-micturition enuresis alarm for individual's having nighttime urinary incontinence may signal the wearer or caregiver, when the bladder reaches 80% of the maximum observed daytime bladder volume.

In one suitable embodiment, the piezoelectric transducer has a frequency in the range of between about 3 MHz and about 5 MHz and is driven by an RF (radiofrequency) transmitter, although in other embodiments, the transducer frequency may vary between about 0.5 MHz and about 5 MHz. The ultrasound burst of the transducer may be generated by, for example, any known means. In one embodiment, a pulse of between about 40 V and about 80 V with about a 30 nano-second rise time and about a 150 nano-second pulse duration has been found suitable to generate the ultrasound burst. The pulse repetition frequency has been found to be acceptable in the range of about approximately 100 Hz although the pulse repetition frequency may typically vary between about 0.01 kHz and about 5 kHz. An exemplary piezoelectric transducer and associated electrical/processing system suitable for use with the present invention is described in more detail in the article "Design of a Miniaturized Ultrasonic Bladder Monitor and Subsequent Preliminary Evaluation on 41 Patients", Petrican, P., et al., *IEEE Transactions on Rehabilitation Engineering*, Vol. 6, No. 1, March 1998, which is incorporated by reference herein.

Figure 5:
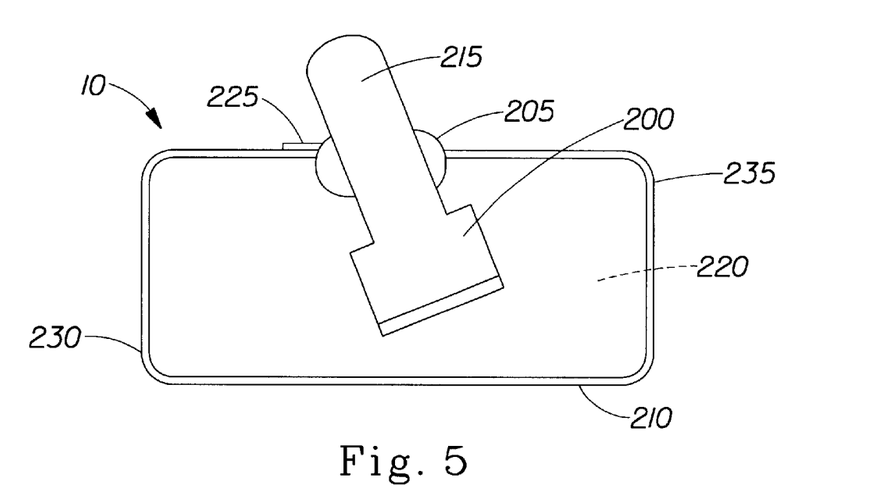
FIG. 5 is a cross-sectional view of one embodiment of the device of the present invention.

In use, the piezoelectric transducer should be oriented appropriately so as to direct the ultrasonic pulse to the target cavity. In order to ensure accuracy in aiming the ultrasonic pulse, in one preferred embodiment of the present invention, as shown in FIG. 5, the device 10 includes an ultrasonic transducer 200 mounted on a base 230. In a preferred embodiment, the ultrasonic transducer 200 is moveably mounted on the base 230. This can be achieved by moveably mounting the transducer 200 directly to the base 230 or by mounting the transducer 200 on a separate element, such as on a tilting stage 205 which is moveably mounted to the base 230. In the embodiment shown in FIG. 5, the tilting stage 205 is disposed within a reservoir 210. The tilting stage 205 includes a handle 215 which allows the user or caregiver to change the angle of orientation of the transducer 200 relative to the reservoir 210 and/or the target body cavity. Thus, the aim of the transducer 200 may be easily and properly adjusted without removing the device 10 from the wearer or moving the entire device 10 relative to the wearer. This eliminates the problems associated with poor aim of the transducer 200 after initial application of the device. The reservoir 210 is preferably filled with a fluid 220 which provides acoustic coupling between the transducer and the reservoir walls. In one embodiment, it has been found that petroleum oils, such as mineral oil, provide suitable acoustic coupling, but other fluids such as silicone oils, gels (e.g., Parker Laboratories Scan Ultrasound gel 11-28 available from Kappa Medical Inc. of Prescott, Ariz.) and other high viscosity oils or other fluids as known in the art will also work acceptably. The reservoir 210 is preferably also acoustically coupled to the wearer's body by a gel or adhesive or has a front elastomer wall which transmits acoustic energy.

The tilting stage 205 and reservoir 210 can be made out of any material, such as plastic, metal, or wood. However, in a preferred embodiment, the walls 235 of the reservoir should be less than about 1.0 mm and preferably less than about 0.5 mm in thickness. The device 10 may also include a locking element 225 to retain the proper orientation of the transducer once the preferred orientation is determined by the user or caregiver. In any case, the tilting stage 205 is preferably hermetically sealed within the reservoir 210 to prevent loss of the fluid 220 during use.

In one preferred embodiment of the present invention, the device 10 functions in a pulse-echo A-mode. Thus, echoes from both the interior and posterior body cavity walls are detected, and the time between the echoes, proportional to the body cavity's linear size in the direction of the ultrasonic beam, is measured and used to estimate the volume or a dimension of the cavity. Such a device 10 preferably further includes electronics including a digital signal processor (DSP). The DSP allows filtering, gating, and thresholding of signals. The output signal corresponding to the linear dimension of the bladder can be transformed into an output signal, such as an audible, tactile, or visual signal, to the user or caregiver.

It is also preferred that the device 10 includes at least two operational modes: a "calibration" mode and a "normal" or "monitoring" mode. In the calibration mode, the user can adjust the tilt of the transducer 200 using the handle 215 until he/she finds the position with the maximum output signal (such as the maximum volume or frequency if the signal is an audible signal), and then can lock the orientation (e.g., proper aim) of the transducer 200 for use in the normal mode. The normal mode is typically used of the device for ongoing body cavity volume monitoring. In the normal mode, the device 10 preferably signals the user or caregiver when the output signal is higher than some pre-set threshold value (for example, the threshold value may be set based on a proportion of the maximum daytime micturition volume, e.g., 80% of maximum observed micturition volume). Further, the threshold value can be fixed or programmable such that it can be changed by the user or caregiver.

Figure 6:
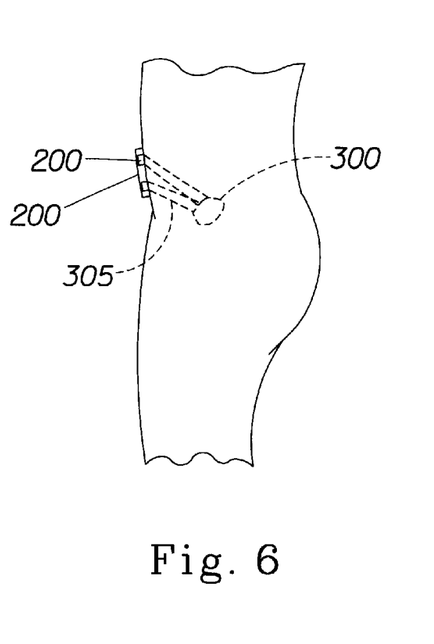
FIG. 6 is a side view of one embodiment of the device of the present invention shown on a wearer.
Figure 6A:
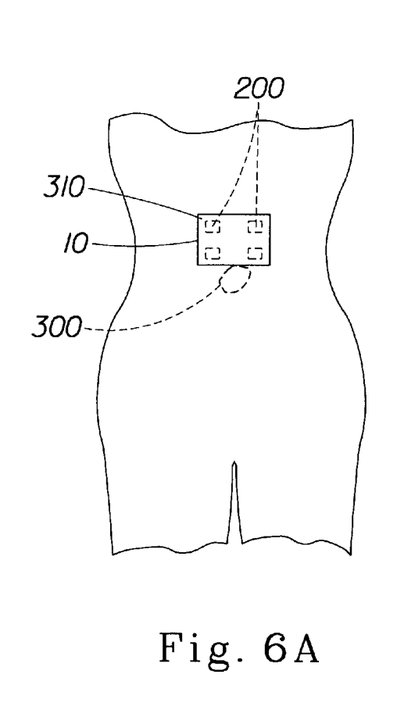
FIG. 6A is a front, plan view of the device of FIG. 6.

In an alternative embodiment, as is shown in FIGS. 6 and 6A, a multiplicity of ultrasonic transducers 200, such as a linear array, may be arranged such that they are aimed at different areas of the body cavity to be monitored. Although any number of transducers 200 can be used as long as more than one signal is generated, it is believed that at least two transducers 200, and preferably, between three and six transducers 200 is preferred to provide sufficient combination of size/area and accuracy. FIG. 6A depicts an exemplary device 10 comprising four ultrasonic transducers 20 in a pad 310 adhered to a subject's abdomen generally over the subject's bladder 300. Each of the transducers 200 is directed toward a different region of the subject's bladder 300 in such a way that displacement or non-optimal orientation of the pad 310 will still allow at least one beam to cross the bladder 300 (exemplary lines of projection are shown in FIG. 6 as dotted lines 305). Preferably, each of the transducers 200 uses the same pulser/receiver circuitry with a multiplexer to aggregate the signals from the transducers. A digital signal processor or the like can be used to compare all of the signals generated by the transducers and determine which signal is the most powerful signal (i.e., maximum measured dimension). The most powerful signal can then be used to most accurately calculate the volume of the subject's bladder 300. This process is relatively fast and simple compared to prior art complex curve fitting algorithms.

The device 10 of the present invention may further comprise a responsive system. A "responsive system" is defined for the purposes of this application as a system that includes a sensor 60 and an actuator that acts upon bodily waste, the wearer, the article, or a component or components thereof when the sensor 60 detects the appropriate triggering input. For example, upon sensing a given body cavity volume, the actuator may effect the release of stored energy or the release or delivery of stored material to perform a responsive function. More specifically, by detecting volumes related to the potential for waste elimination, a responsive system in the article may be triggered to prepare for the event or to signal the caregiver or the wearer of the impending event. This allows construction of articles in which the waste-management technology is initially hidden or unobtrusive, but which is available at, or just before, the moment of need and/or in which the article may provide the caregiver or the wearer the opportunity to prepare for an event in advance. If the device 10 comprises more than one sensor or a sensor that detects more than one input, each actuator may be triggered by a different sensor and/or signals, or different actuators may be triggered by different sensors and/or signals. Alternatively, one sensor and/or signal may trigger multiple actuators.

In certain preferred embodiments of the present invention, the responsive system may include an actuator, such as signal mechanism 90, that alerts the caretaker or the wearer of an impending event such as a urination or a defecation.

Any audible, visual, or telemetry based signal mechanism as known in the art may be suitable for use in the present invention. If the responsive system alerts the caretaker, for example, the caretaker may prepare to change the article to minimize the amount of time that the bodily waste is in contact with the skin of the wearer, may ensure that a bedpan or an absorbent article is in place to contain the bodily waste when it is eliminated, or may aid the wearer in getting to the bathroom before the elimination of the bodily waste. In another embodiment, the responsive system may actually stimulate a portion of the wearer's anatomy in response to the system's sensing of the impending event. Thus, the responsive system can, for example, stimulate the wearer to contract the urethral or anal sphincter muscle prior to an impending defecation or urination. This may provide the wearer with enough time to make it to a toilet or to fit him or herself with an appropriate absorbent or other waste receiving article prior to the waste actually leaving the body.

The actuator may be disposed in and/or operatively connected to any portion of the device 10 or other article that will allow the actuator to perform a responsive function upon the bodily waste, the wearer, the article, or a component thereof. In a diaper, for example, the actuator may be located in the front waist region, the rear waist region or the crotch region of article, and may be integral with, disposed adjacent to or joined to a component of the chassis, the topsheet, the backsheet, the absorbent core, side panels, leg cuffs, a waist feature, a fastening system, the longitudinal or end edges, etc. The actuator may also be completely contained within the article, may have a portion located in the article and a portion located outside the article, or may be completely external to the article. Further, the actuator may be integral with the article, or may be installed by the caretaker or the wearer.

The device 10 or article may also include a controller. A "controller" is defined for the purposes of this application as a device that receives an input from a sensor and determines if one or more actions are to be taken.

Suitable responsive systems are described in U.S. Pat. No. 6,093,869, entitled "Disposable Article Having A Responsive System Including A Feedback Control Loop", and U.S. patent application Ser. No. 09/106,424 entitled "Disposable Article Having A Discontinuous Responsive System" filed on Jun. 29, 1998, which has been allowed; and Ser. No. 09/106,225 entitled "Disposable Article Having A Responsive System Including A Mechanical Actuator" filed on Jun. 29, 1998 (P&G Case Number 7199), each of which is incorporated herein by reference.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention. Also, although the present invention is illustrated and described primarily with respect to a device, particularly one wearable on the body, the present invention is not limited to this embodiment. The present invention may also be used, for example, in disposable articles that are applied directly to a wearer (e.g., to the perianal or perineal regions of the wearer), such as diapers, diaper inserts, training pants, feminine napkins, disposable briefs, swim pants, and waste bags.

What is claimed is:

1. A garment comprising a device adapted to measure a volume of a body cavity of a wearer, the device comprising at least one sensor and a signal mechanism adapted to provide a signal to the wearer or a caregiver once the volume of the body cavity reaches a predetermined threshold.

2. The garment of claim 1 wherein the sensor includes an ultrasonic transducer.

3. The garment of claim 2 wherein the transducer has a frequency in the range of about 0.5 MHz to about 5 MHz.

4. The garment of claim 3 wherein the transducer has a frequency in the range of about 3 MHz to about 5 MHz.

5. The garment of claim 1 wherein the body cavity has opposed walls and the sensor is adapted to detect a distance between the opposed walls.

6. The garment of claim 5 wherein the device correlates the distance between the opposed walls to a calculated body cavity volume.

7. The garment of claim 6 wherein the device comprises at least two sensors directed toward different regions of the body cavity and adapted to detect distances between the opposed walls in the different regions.

8. The garment of claim 7 wherein the device is adapted to measure the volume of the body cavity using a greatest of the detected distances between the opposed walls.

9. The garment of claim 1 wherein the sensor is moveably mounted on a base so as to facilitate aiming of the sensor toward the body cavity.

10. The garment of claim 9 wherein the base comprises a reservoir containing a fluid.

11. The garment of claim 10 wherein at least a portion of the sensor is hermetically sealed within the reservoir.

12. The garment of claim 9 wherein the device includes a locking element adapted to retain the sensor in a particular orientation with respect to the base.

13. The garment of claim 1 wherein the body cavity is a rectum, a bladder, or a colon.

14. The garment of claim 13 wherein the body cavity is the bladder.

15. The garment of claim 14 wherein the device is adapted to serve as a pre-micturition enuresis alarm.

16. The garment of claim 1 wherein the device measures the volume at a predefined interval.

17. The garment of claim 1 wherein the signal mechanism provides a signal in the form of an audible signal, a tactile signal, or a visual signal.

18. The garment of claim 17 wherein the signal is provided in a form and at a location so as to alert the wearer.

19. The garment of claim 17 wherein the signal is provided in a form and at a location so as to alert the caregiver.

20. The garment of claim 1 wherein the predetermined threshold volume is about 80 percent of an observed minimum voiding volume.

21. The garment of claim 1 wherein the garment is selected from the group including absorbent articles, diapers, training pants, swim pants, incontinence briefs, and undergarments.

22. The garment of claim 21 wherein the garment is an absorbent article including a backsheet and an absorbent core joined to the backsheet.

* * * * *

UNITED STATES PATENT AND TRADEMARK OFFICE
CERTIFICATE OF CORRECTION

PATENT NO. : 6,359,190 B1
DATED : March 19, 2002
INVENTOR(S) : Evgeny Ter-Ovanesyan et al.

It is certified that error appears in the above-identified patent and that said Letters Patent is hereby corrected as shown below:

Column 1,
Line 52, delete "bladder, A" and insert therefor -- bladder. A --.

Column 5,
Lines 5 and 6, delete "Dow Coming" and insert therefor -- Dow Corning --.

Signed and Sealed this

Seventeenth Day of August, 2004

JON W. DUDAS
*Acting Director of the United States Patent and Trademark Office*